United States Patent [19]

Lundblad

[11] Patent Number: 4,579,109

[45] Date of Patent: Apr. 1, 1986

[54] APPARATUS FOR TREATING BACK AILMENTS

[76] Inventor: Leif Lundblad, Häradsvägen 102, S-141 41 Huddinge, Sweden

[21] Appl. No.: 621,910

[22] PCT Filed: Nov. 18, 1983

[86] PCT No.: PCT/SE83/00405

§ 371 Date: Jun. 8, 1984

§ 102(e) Date: Jun. 8, 1984

[87] PCT Pub. No.: WO84/02075

PCT Pub. Date: Jun. 7, 1984

[30] Foreign Application Priority Data

| | | | |
|---|---|---|---|
| Nov. 29, 1982 | [SE] | Sweden | 8206799 |
| Nov. 29, 1982 | [SE] | Sweden | 8206800 |
| Nov. 29, 1982 | [SE] | Sweden | 8206801 |
| Nov. 21, 1983 | [ES] | Spain | 13993 |
| Nov. 28, 1983 | [IT] | Italy | 23915 A/83 |

[51] Int. Cl.[4] .......... A61F 5/00

[52] U.S. Cl. .......... 128/72; 128/71; 128/75

[58] Field of Search .......... 128/71, 72, 70, 69, 128/73, 74, 75, 33, 34

[56] References Cited

U.S. PATENT DOCUMENTS

| | | | |
|---|---|---|---|
| 1,076,475 | 10/1913 | Albright | 128/74 |
| 2,693,796 | 11/1954 | Warner | 128/70 |
| 2,908,271 | 10/1959 | Ware | 128/33 |
| 3,282,584 | 11/1966 | Anderson | 128/73 |
| 3,640,272 | 2/1972 | Hussey | 128/33 |
| 3,771,518 | 11/1973 | Greissing | 128/71 |
| 4,258,707 | 3/1981 | Lettinga | 128/75 |
| 4,266,537 | 5/1981 | Bonin, Jr. et al. | 128/75 |
| 4,271,830 | 6/1981 | Moon | 128/72 |
| 4,378,791 | 4/1983 | Sarrell | 128/71 |
| 4,508,109 | 4/1985 | Saunders | 128/75 |

FOREIGN PATENT DOCUMENTS

| | | | |
|---|---|---|---|
| 83/00620 | 3/1983 | PCT Int'l Appl. | 128/75 |

*Primary Examiner*—Gene Mancene
*Assistant Examiner*—Cary E. Stone
*Attorney, Agent, or Firm*—Kinzer, Plyer, Dorn & McEachran

[57] ABSTRACT

An apparatus for treating back ailments includes patient support table (10) for supporting a patient in a horizontal, lying position; a first tension take-up belt (12) arranged to pass around the pelvis area of a patient; a second tension take-up belt (14) arranged to pass around the chest of a patient; tensioning belts (131, 131'; 132, 132') arranged for connection to a selected one of the first and the second tension take-up belt (12, 14); carriage (11) which are intended to support the pelvis region or the chest region of the patient, and which can be readily moved relative to the patient support table (10); a movably arranged and vertically adjustable lumbar support (15) mounted on the patient support table; and drives (141, 142, 143, 145) for activating the tensioning belts, and the readily movable carriage. The apparatus is also provided with movement program control unit (18) through which a diagnosis of the patient's back can be made, treatment carried out in accordance with a set program of movements, and the result of the treatment analyzed.

15 Claims, 7 Drawing Figures

APPARATUS FOR TREATING BACK AILMENTS

TECHNICAL FIELD

The present invention relates to apparatus for treating back ailments, and more particularly to an apparatus of the kind which includes patient support means for supporting a patient in a horizontal, lying position; a first tension take-up means arranged to pass around the pelvis area of a patient; a second tension take-up means arranged to pass around the chest of a patient; tensioning means arranged for connection to a selected one of said first and said second tension take-up means; carriage means which are intended to support the pelvis region or the chest region of the patient, and which can be readily moved relative to said support means; a movably arranged and vertically adjustable lumbar support means mounted on the patient support means; and drive means for activating the tensioning means, and the readily movable carriage means.

BACKGROUND ART

Various apparatus for treating back ailments are known to the art, these apparatus being of widely different designs and operational modes.

One such apparatus includes a movable support surface intended to support the pelvis region of a patient, said support means being arranged for rotation about a first horizontal axis, about a second horizontal axis, and about a vertical axis; a fixed support surface for supporting the chest of the patient; and lumbar support means. It is not possible, however, to apply traction with such an apparatus, which is a serious disadvantage, since traction must be considered an important part of a complete program for successfully treating back ailments. Neither are means provided which are capable of regulating the height of the lumbar support means during the course of treatment in question, it would appear that the support means can only be set in an initial position corresponding to the shape of the back of a patient undergoing treatment.

Another known apparatus includes a fixed support for supporting the chest area of a patient; lumbar support means which are rotatable about a vertical axis, so that said lumbar support means can accompany movement of the patient in the longitudinal direction of the apparatus; and movable pelvis support means, which can be imparted a translatory movement in the longitudinal direction of the apparatus (and of the patient). Consequently, it is not possible with this known apparatus to execute any form of rotary movement, other than small movements conforming to a pre-arranged program.

A further known apparatus of the aforesaid kind includes two movable support means which are arranged one behind the other and which can be rotated about one and the same axis but in mutually different directions, so as to move in an oscillatory fashion, thereby to turn or twist the back of the patient of some extent. The apparatus has no means for supporting the small of the back, i.e. the lumbar region of the patient, and cannot subject the patient to traction. Moreover, the turning or twisting (torsion) action is limited to a single axis of rotation.

These and similar apparatus normally have a very limited healing effect on the back ailments of the patient, and when used wrongly can sometimes be very dangerous.

Accordingly, it is a first object of this invention to provide an apparatus for treating back ailments which will afford the best possible treatment with the least possible discomfort to the patient.

Another object is to provide an apparatus of the kind described with which a diagnosis can be made, treatment carried out, and the result of the treatment analysed, in a manner such that the back ailment of a patient can be charted and treated correctly, optionally through the patient's own activities, and in all events so that it is established what should (or can) be done, and so that treatment is effected at the correct locations and at suitable moments in time.

DISCLOSURE OF THE INVENTION

In accordance with the invention, these objects are achieved by means of an apparatus according to the invention which is characterized in that the apparatus further includes a movement program control unit which is arranged to initiate and to control a desired sequence of movements in accordance with a program entered therein, said unit including means for registering and recording the reactions of and the sensations experienced by the patient as said patient executes the movements in said program, and operator or patient controlled means for halting all movement of the apparatus, irrespective of the point reached in the program.

The control unit preferably includes a movement selector panel and a movement control panel which are coupled to the drive means in a manner such that a patient suffering from a back ailment can be systematically subjected to an initial diagnosis; that a movement program for the patient's back can be established on the basis of said diagnosis; and that the status of the patient's back subsequent to being treated can be recorded and compared with the status of said patient's back prior to carrying out said treatment.

The diagnosis is conveniently carried out in accordance with a previously compiled program stored in data processing means incorporated in the control unit and, following instructions given by the doctor or physiotherapist, can be carried out by the patient himself-/herself, by manipulation of a control means on the control panel. The program includes instructions for testing the ability of the patient to move the small of his back, to bend sideways, and to turn.

The movement program is suitably compiled by a doctor, and when required is initiated through the selector panel in the control unit. The movement program can be optionally selected automatically in the data processor, by initiating a previously inserted, fixed program, while observing the result of the initial diagnosis.

By means of recording means (buttons) arranged in the control panel for indicating or recording sensations of pain during body movement (e.g. traction), the patient is himself able to influence the program, and during the course of treatment cause factors to be recorded which, when taken together, present a true picture of the state of the patient's back. This enables the patient to undergo treatment while in a quiet and relaxed condition.

So that the invention will be more readily understood and further features thereof made apparent, a number of embodiments will now be described with reference to the accompanying schematic drawings, in which FIG. 1 illustrates an apparatus for treating back ailments and having a movement program control in accordance with the invention.

PREFERRED EMBODIMENTS OF THE INVENTION

Figure 1:
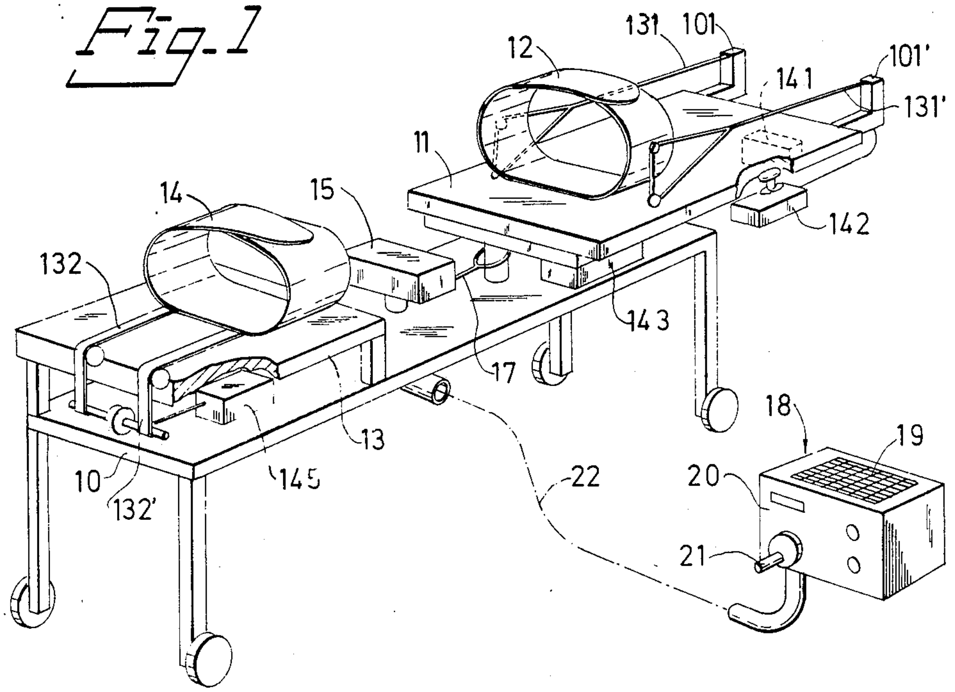

The apparatus illustrated in FIG. 1 includes a patient support surface 10 for supporting a patient in a horizontal lying position. Arranged for ready movement relative to the support surface 10 is a carriage means 11, which is intended to support either the pelvis region of the patient or the chest region thereof. As will be made more apparent later on, the carriage means 11 is arranged for translatory movement and rotational or pivotal movement modes about respective axes, and is driven by drive means 141, which may have the form of a motor.

Mounted on the carriage means 11 is a first tension take-up means in the form of a belt 12 which in this embodiment is intended to support the pelvis region of the patient, and which is tensioned by means of tensioning means 131—131′, driven by motor 142.

In order to support the chest of a patient during a course of treatment, there is arranged on the support means 10 at some distance from the carriage means 11, a chest support means 13 which has arranged thereon a second tension take-up means in the form of a belt 14, which is arranged to encircle the chest of said patient and which is tensioned by straps 132—132′, driven by motor 145. In the illustrated embodiment the chest support means 13 is stationary relative to the patient support means 10.

Arranged between the pelvis and chest support means 11 and 13 is a movable and vertically adjustable lumbar support means 15. By lumbar is meant here, and in the following, as well as in the aforegoing, that area of the body normally referred to as the "small of the back".

The first tension take-up means, i.e. the belt 12 is placed under tension, e.g. for traction purposes, by means of the tensioning means 131 and 131′ having the form of cables which extend to a respective post 101 and 101′ located at one end of the support means 10, and which are operated by said drive means 142, while the second tension take-up means 14, e.g. for holding the chest firmly on the chest support, has the form of tensioning straps 132, 132′, which are operated by drive means 145.

The reference 17 identifies a coupling means coacting between the lumbar support means 15 and the carriage means 11 for a purpose which will hereinafter be made apparent.

As will be seen from FIG. 1, each of the drive means 141, 142, 143, 145 is connected to a movement program control unit 18, which includes a movement sequence selector panel 19 and a control panel 20, on which there is arranged a program control means, in the form of a knob or dial 21. Control-signal lines leading to respective drive means 141–145 are shown by chain line 22.

The drive means 141, 142, 143, 145 are designed and operationally connected to the control unit 18 in a manner such that when a given sequence of movements is initiated, e.g. translation, through the selector panel 19, and the knob or dial 21 is turned clockwise, the translatory movements are carried out successively, while when the knob is turned counter-clockwise, the sequence of movements is effected in the reverse order.

The knob 21 illustrated in FIG. 1 can be replaced with, for example, a lever having three operational states, namely a right-hand state, an intermediate state, and a left-hand state; or with a keyboard having a right-hand button, a left-hand button, and an intermediate button. All three embodiments form control means which can be easily reached and manipulated by the patient. (For the sake of illustration, the control unit 18 has been drawn slightly to one side of the remainder of the apparatus.)

The control unit 18 illustrated in FIG. 1 includes a data processor (not shown in the Figure) in which is stored a programmed sequence of movements which can be initiated through the selector panel 19. The control panel 20 includes, in addition to the control means 21 (the knob), an alarm button 23, and a recording and/or indicating means (24) for recording sensations of pain experienced during the sequence of movements being carried out by the patient (e.g. during traction), said recording means being so arranged that when activated by the patient to record said pain sensations the program is either stopped, or a jump is made to a further state or part-program thereof.

The selector panel 19 includes a keyboard 200–201 for the selection of such movements as translation, rotation and turning or pivoting of the readily movable carriage means 11, and for setting the limits to which said movements shall be made; and for setting the vertical translatory movement of the lumbar support means 15 and for setting the limits to which such movement shall be made. An array of lamps 202–203 is arranged to indicate the positions and values (202) in question, and momentary symbolic images (203) of the sequence of movements being carried out.

The unit 202 includes digital instruments for reading-off the pressure exerted on the lumbar support means 15 (in Newtons, three figures); the height of said lumbar support means 15 (in centimeters, two figures), the turning or pivot angle (in degrees, two figures), rotation (in degrees, two figures), traction force (in Newtons, three figures), and time (in minutes, three figures). The unit 203 includes lamps having symbols which identify the function in question and which illuminate when a corresponding button on the keyboard 200 is pressed.

The control unit 18 can be swung to any position desired by the patient or the physiotherapist.

The control unit 18 also includes a register 25 which is arranged to be activated at regular intervals, when the patient activates the recording means 24, and at the end of each movement sequence, e.g. translation, for registration of relevant factors, such as, for example, the tension force in the tensioning means 131—131′, the pressure exerted against said lumbar support means 15, etc.

The data processor incorporated in the control unit 18 is arranged to make a comparison between the factors registered by the register 25 and deriving from an initial mobility diagnosis—made at the beginning of a course of treatment—with factors deriving from a movement program carried out at the end of said course of treatment, thereby enabling a clear and concise picture of the result of said treatment to be obtained.

In the aforegoing it has been assumed that the pelvis support means 11 is movable and the chest support means 13 is stationary, and that the tension forces required for traction are generated by the tensioning means 131—131', while the tensioning means 132—132' are intended for holding the patient's chest firmly to the chest support means. If considered suitable, the pelvis support means 11 can bd stationary and the chest support means 13 movable, wherewith the tension force required for traction is obtained through the take-up means 14. In this respect the tensioning means 132—132' is suitably modified to coincide, for example, with the illustrated tensioning means 131—131'. Cables 231-234 required for transferring data to and from the various units are located between the selector panel 19, the control panel 20, and the register 25. Data relating to activation by the patient of knob 21, the recording means 24, and the alarm button 23 is transmitted from the control panel 20 to the selector panel 19 (with data processor) over cable 231.

Signals containing data relating to instructions for the patient are transmitted from the selector panel 19 to the control unit 20 over cable 232. These instructions are presented on a display 214, and may instruct the patient either to turn the knob 21 or to wait (rest), or may inform him that the course of treatment has been concluded.

Control signals relating to the registration of such data as time-recording, recording of angular values when turning and rotating respective support means, recording of tension and pressure values etc., are transmitted from the selector panel 19 to the register 25 over cable 233.

Signals containing data relating to activation by the patient of the knob, the recording means 24 and the alarm button 23 are transmitted from the control panel 20 to the register 25 over cable 234.

In principle, the aforedescribed apparatus has three different modes of use, namely manual use; use in accordance with an individual program; or use in accordance with a standard program.

When used manually, a given function, e.g. traction, is selected through the keyboard 200. The maximum tension force is set by means of keyboard 201, and the value selected is shown on the array-lamps 201. The function selected is initiated by turning the knob 21; this being done by either the patient or the physiotherapist. When the knob is turned to the right, the tensioning force is produced through the tensioning means 131—131', while the tension in the tensioning means is relaxed when turning the knob to the left.

When the apparatus is used in conjunction with an individual program, there is first made an initial diagnosis, to establish an original point of departure with respect to the course of treatment adopted, i.e. the patient carries out in said apparatus a program entailing movement of the small of the back, rotational movements and turning movements, to establish the degree of mobility of the patient. The doctor or physiotherapist then compiles a program of treatment, which is entered into the memory of the data processor of the control unit, through the selector panel 19. This program is stored, and initiated when the patient reports for treatment. The patient can carry out the treatment himself, by means of the knob 21. When the knob is turned to the right, the program is wound forwards, and is wound backwards when the knob is turned to the left.

As beforementioned, as the program progresses, the patient obtains through the display 214 such instructions as "turn the knob" or "wait". The patient signals the feeling of pain by pressing the knob 24.

When using the apparatus in conjunction with a standard program, there is used a part-program which has been previously inserted into the data processor and which can be initiated through the selector panel 19. The data processor may also be programmed to select the requisite part-program itself, on the basis of the diagnosis carried out.

By way of summary, a course of treatment can have the following pattern:

1. The patient himself/herself records factors relating to his/her back ailment on a form intended therefor.
2. The doctor or physiotherapist investigates the ability of the patient to bend and turn.
3. A statistical diagnosis is made in the apparatus, during which the height of the small of the back is measured, together with the ability of the patient to turn or bend sideways (right and left) and to turn in two directions.
4. A suitable program of treatment is compiled.
5. The patient "runs" through the program himself/herself, whereupon data of interest is registered automatically.
6. A fresh statistical diagnosis is carried out on the apparatus and compared with the initial diagnosis.
7. A written record of the result of the comparison is obtained from the register 25, together with suggestions for further treatment.

The first mentioned comparison made in the data processor between the initial mobility diagnosis and the concluded program can also include factors of particular interest recorded from the actual treatment carried out such as the maximum extent to which the patient is able to bend, turn etc. without undue discomfort.

In order to ensure that the position of the lumbar support means 15 conforms more readily to the positions of other apparatus components, so that the patient suffers no side effects, the lumbar support means 15 according to one embodiment of the invention is so arranged that when the carriage means 11 moves in accordance with a pre-arranged program, movement of the lumbar support means 15 is adapted in a manner which is determined by and which conforms to the natural position of the small of the back of said patient, i.e. the lumbar region thereof. This is effected, inter alia, by means of a mechanical coupling 17, 26-28 between the lumbar support means 15 and the carriage means 11 and by the design of said lumbar support means 15, such that when the carriage means 11 executes a horizontal translatory or turning movement, the lumbar support means 15 will adopt the position determined by and conforming to the natural attitude of the small of the back of said patient during respective movements, while when the carriage means 11 executes a rotary movement about a horizontal axis, the lumbar support means 15 will take the same position as the chest support means 13 during the whole of said rotary movement.

In accordance with this embodiment, in those cases when the carriage means 11 forms the pelvis support means, the lumbar support means 15 will accompany the translatory and turning movements of the pelvis support to a greater or lesser extent, but will remain stationary during the rotary movement thereof. On the other hand, when the carriage means 11 forms the means 13 for supporting the chest region of the patient, the lumbar support means 15 will accompany the carriage means/chest support means throughout the whole of its rotary movement.

Figure 3:
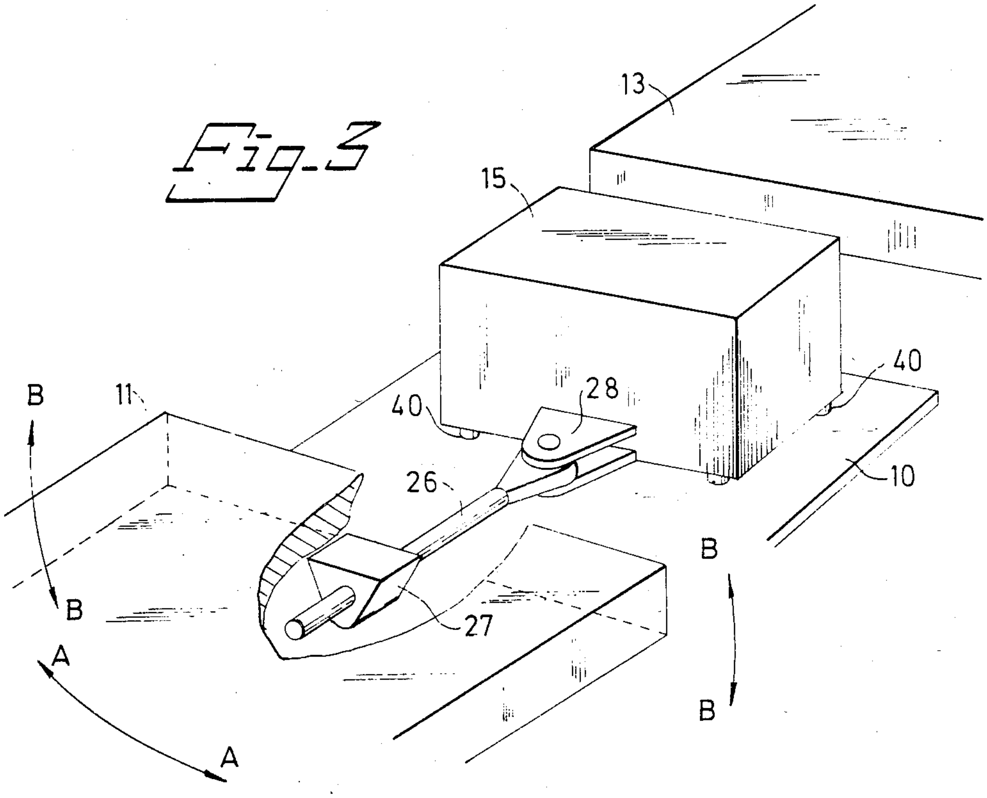
FIG. 3 illustrates an embodiment of a coupling means between the lumbar support means and the carriage means; and also illustrates an embodiment of a lumbar support guide means.
Figure 2:
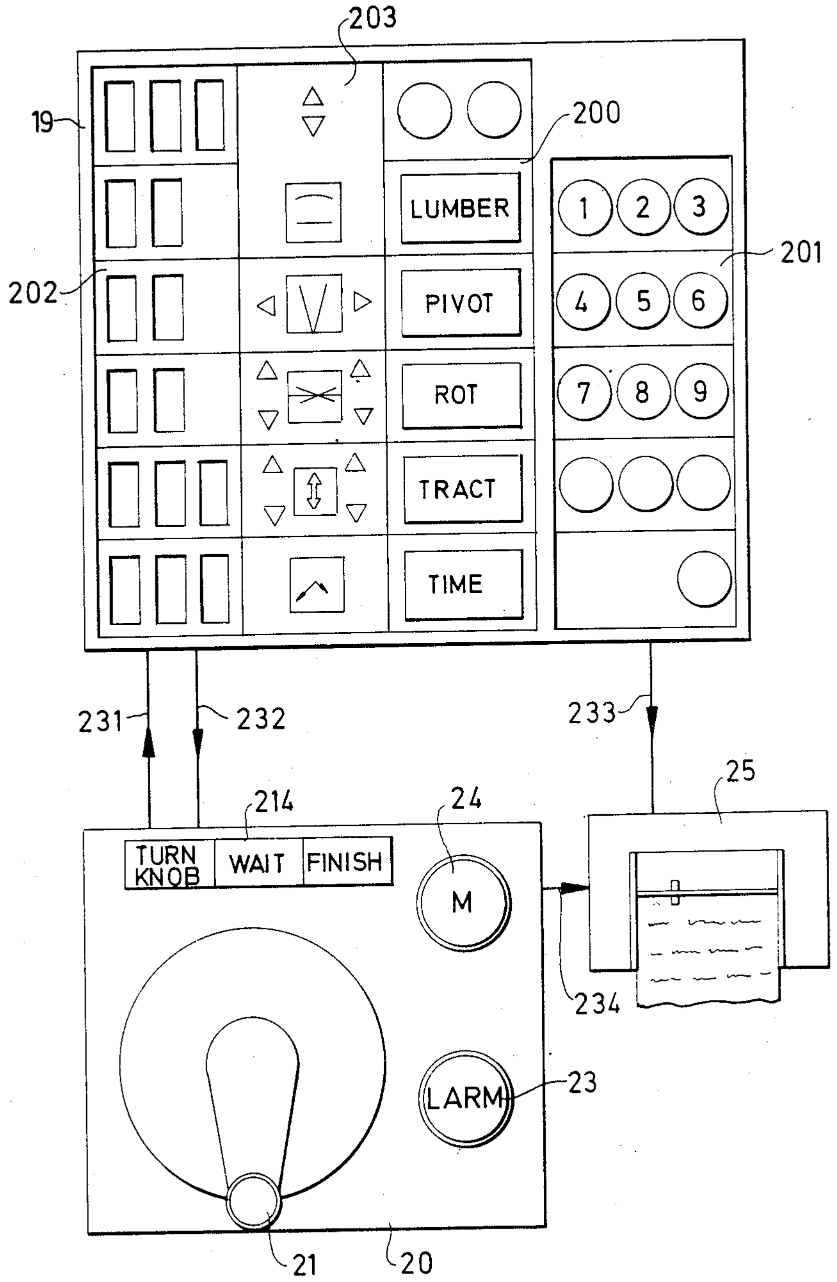
FIG. 2 illustrates the movement program control unit in more detail.

As will be seen more clearly from FIG. 3, said mechanical coupling 17 (FIG. 1) is a combined slide and pivot coupling and comprises a rod 26 which is freely slidable at one end thereof in the longitudinal direction of the apparatus in a bush 27 which is fixed to the carriage means 11. The other end of the rod 26 is mounted for free pivotal movement in a bracket structure 28 attached to the lumbar support means 15.

The lumbar support means 15 of the FIG. 3 embodiment is arranged on rollers or castors 40, so as to be freely movable relative to the patient support means 10. As beforementioned, the height of the lumbar support means 15 above the patient support means 10 is adjustable.

The arrows A-A indicate the turning or pivoting movements executed by the carriage means 11 about a vertical axis, and the arrows B-B indicate the rotary movements of said carriage means about a horizontal axis. As a result of the extension of the lumbar support means 15 in the transverse direction of the apparatus, i.e. the distance between the rollers 40 in the transverse direction, said rollers will act as a mechanical guide means to positively prevent the lumbar support means from accompanying the rotary movement of the carriage means 11 about said horizontal axis. The ability of the rod 26 to slide freely relative to the bush 27 is also contributory in this respect. Another method of mechanically guiding the lumbar support means for the aforesaid end, is to arrange a rectangular recess slightly beneath the uppermost surface of the support, and to insert in said recess a guide means which is fixed relative to the patient support means 10 and which permits freedom of movement in the horizontal plane, within required limits, but which opposes any tendency of the lumbar support means to rotate about a horizontal axis.

In the foregoing it has been assumed that it is the pelvis support means which forms the carriage means 11. Although this is considered to be the most practical, there is nothing to prevent the pelvis support means from being permanently fixed, and allowing the chest support means to form said movable carriage means, as beforementioned. In this latter case, however, the mechanical guide must be such as to enable the lumbar support means 15 to accompany the rotary movement of the carriage means 11, for example by providing the support and said carriage means with a common supporting surface, while being guided by the couplings 27–26–28.

Thus, when the patient is under traction, the lumbar support means 15, through the rod and bush coupling 26 and 27, will take a position conforming to the natural position of the patient's lumbar region, as the carriage moves relative to the patient support means 10. On the other hand, when the carriage means is pivoted or swung about a horizontal axis, the lumbar support means will accompany said pivotal movement through the agency of the rod and link bracket coupling 26 and 28 and the rollers 40, to an extent determined by, and conforming to the natural position of the patient's lumbar region, As beforementioned, the rollers 40 form a positive guide means which when the carriage means 11 executes a rotational movement about a horizontal axis, cause the lumbar support means to take the same position relative to the chest support means 14, during the whole of said rotational movement. All three conditions placed on the lumbar support through the coupling 26–28 and the guide means 40 ensure that the lumbar support means will always take a position which conforms to the natural position of the small of the patient's back.

Figure 4:
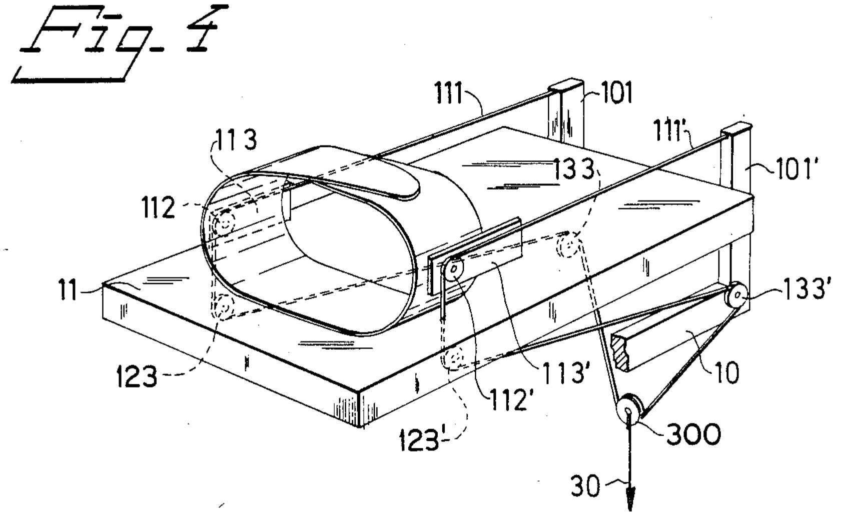
FIG. 4 illustrates a first embodiment of a tension control means, and shows the tension take-up means intended for the pelvis region of the patient.
Figure 5:
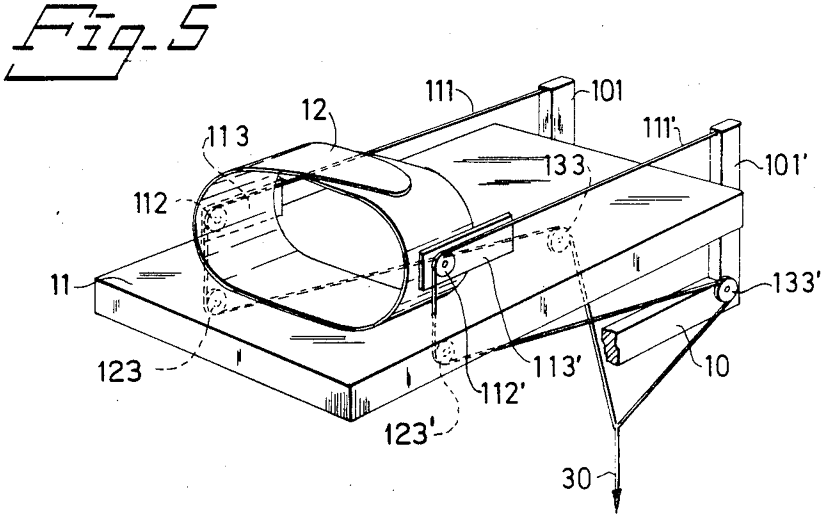
FIG. 5 is a second embodiment of a tension control means.
Figure 6:
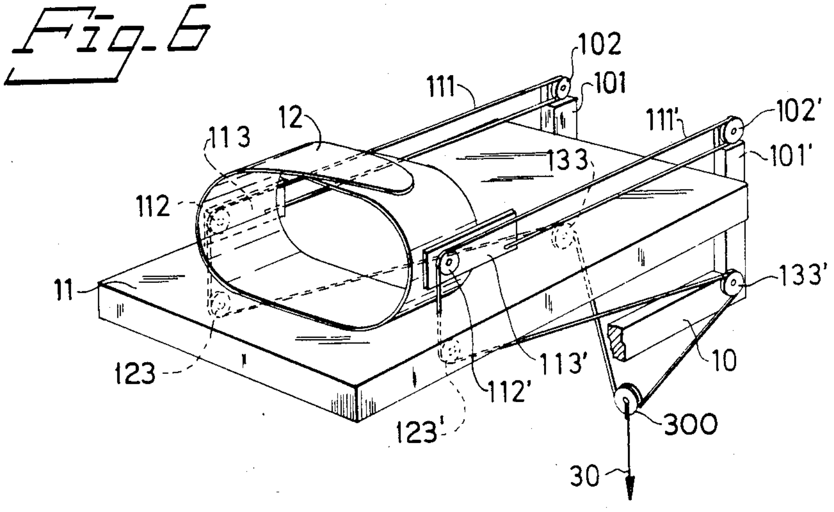
FIG. 6 is a third embodiment and FIG. 7 is a fourth embodiment of a tension control means.

FIGS. 4, 5 and 6 illustrate alternative embodiments of tension control means, by which the patient can be held firmly to the pelvis support means and to the chest support means, without placing undue strain on the patient's back.

In the embodiment illustrated in FIG. 4, the belt of the first tension take-up means 12 has mounted thereon a first pair of pulleys 112, 112', while the movable carriage means 11 has mounted thereon a second pair of pulleys 123, 123'. A third pair of pulleys 133, 133' is mounted on the patient support means 10. The pulley pair 123, 123' is mounted on the underside of the movable carriage 11, approximately immediately beneath the pulley pair 112, 112', while the pulley pair 133, 133' is mounted at one end of the patient support means 10, adjacent the post pair 101,101'.

The belt is connected to the belt tensioning means 30 via a line arrangement, which in the illustrated embodiment comprises line portions 111, 111' extending from said belt to a respective post 101 and 101'.

Each of the line portions 111, 111' connects one of said first pulleys, e.g. 112, with one of the second pulleys 123 and one of said third pulleys 133. One end of each line portion is secured to a tensioning means 30, while the remaining end of one of said line portions is secured to the patient support means, namely to the post 101 for the line 111 (Correspondingly, the line portion 111' connects the wheel or roller 112' with the pulley 123' and the pulley 133', and one end of the line portion is secured to the tensioning means 30 and the remaining end to the post 101'.) The tensioning means 30 has a grooved wheel 300 around which said remaining ends, the co-linking ends, of the line portions 111, 111' are passed. When the tensioning means 30 is subjected to a tension force, the forces acting in the lines will be equalized through the action of the wheel 300, while possibly turning the carriage means 11 at the same time.

FIG. 5 illustrates a modification of the embodiment illustrated in FIG. 4, in which the force-equalizing wheel 300 has been omitted from the tensioning means 30. Thus, the lower ends of the line portions 111, 111' are secured directly to the tensioning means 30, which means that each line has a constant length during the course of the treatment. Consequently, the tension forces in the two lines may be mutually different and may vary during the course of said treatment.

A further embodiment is illustrated in FIG. 6. In addition to the apparatus components described in the aforegoing, the embodiment according to FIG. 6 includes a fourth pair of pulleys 102, 102', which are mounted on the posts 101, 101'. Attached to the sides of the belt belonging to the tension take-up means 12 are rigid plates 113, 113'. These plates extend over the whole width of the belt and somewhat beyond the edge of the belt facing the foot-end of the support means (furthest away from the reader). One end of the line portion 111 is attached to the plate 113 and extends around the pulleys 102, 112, 123 and 133 in the order just mentioned, while one end of the line portion 111' is attached to the plate 113' and extends around the pulleys 102', 112', 123' and 133' in that order. The remaining ends of the line portions meet around the grooved wheel 300 in the tensioning means. Thus, two parts of the line 111 and 111' pass between a respective plate 113 and 113' and a respective pulley 102 and 102', which has been found important with respect to the application of the tensioning force.

In the aforegoing it has been assumed that it is the pelvis region of the patient which is to be pulled, while the chest region is firmly anchored to the support means. In principle the reverse may be the case, so that it is the chest region which is pulled. This reversal, however, necessitates modification of the illustrated arrangements, although while retaining the principles thereof.

The members 102, 102', 112, 112', 123, 123' and 133, 133' have been shown and described as pulleys, although, as will be understood, there members may have the form of equivalents devices, such as rollers, eyes, etc. which ensure that the lines run freely. The members 111, 111' may also comprise straps, bands or the like.

The embodiment according to FIG. 6 can be modified by omitting the wheel 300, in which case each of the line portions 111, 111' has the end in question securely connected to the tensioning means 30, i.e. in the manner indicated in FIG. 5.

Figure 7:
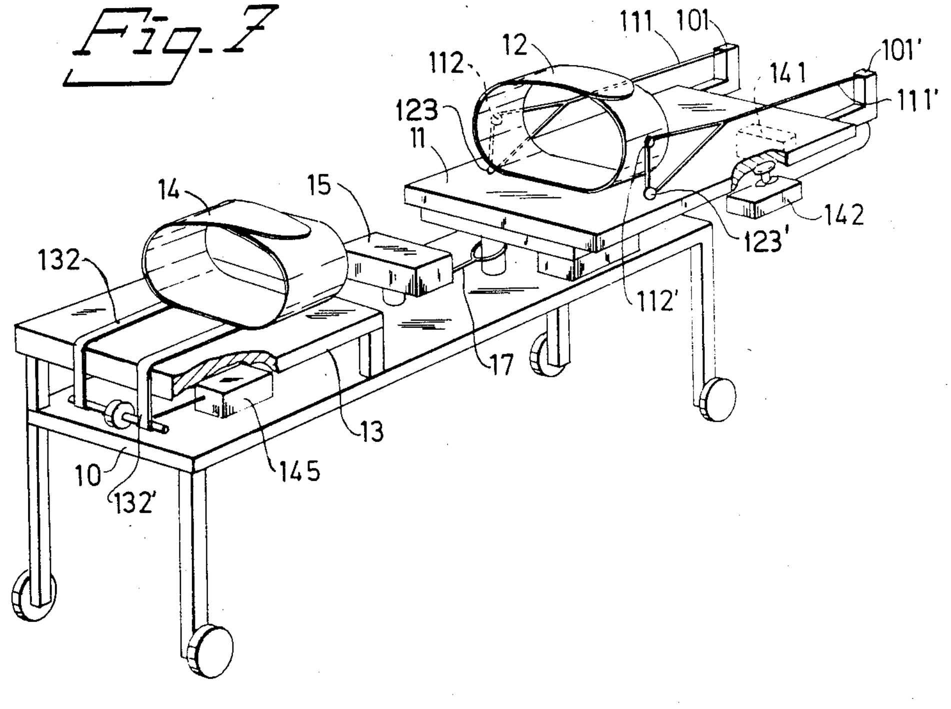

FIG. 7 illustrates a simplified version of the tension control means according to the invention. In this embodiment belt 12 (or the belt 14) is provided with a first pair of pulleys 112,112', while a second pair of pulleys is mounted on the movable carriage means 11. A line arrangement comprises line portions 111,111' and connects respective pulleys of the first pair to respective pulleys of the second pair. One end of the line arrangement is conncected to the tensioning means 30 or 141, while the other end is fixedly arranged relative to patient support means 10, the first or second straps 12,14, or to the line itself.

I claim:

1. An apparatus for treating back ailments, and more particularly an apparatus of the kind which includes patient support means (10) for supporting a patient in a horizontal, lying position; a first tension take-up means (12) arranged to pass around the pelvis area of a patient; a second tension take-up means (14) arranged to pass around the chest of a patient; tensioning means (131, 131'; 132, 132'; 111, 111'; 30) arranged for connection to a selected one of said first and said second tension take-up means (12,14); carriage means (11) intended to support the pelvis region or the chest region of the patient, and which can be readily moved relative to said patient support means (10), a movably arranged and vertically adjustable lumbar support means (15) mounted on said patient support means (10); and drive means (141,142,143,145) for activating said tensioning means and the readily movable carriage means according to selected program instructions, characterized in that the apparatus includes a movement program control unit (18) arranged to control said drive means (141,142,143, 145) to initiate and to control a selected sequence of movements in accordance with a program entered therein, said control unit (18) including: a movement sequence selector panel (19) having means (200–201) for selecting translatory, rotational and pivotal movement of the carriage means (11), for setting the limits of such movements, and for restricting the vertical movement of the lumbar support means (15); a control panel (20) which is coupled to the selector panel (19) and which has arranged thereon a control means (21) for controlling the sequence of movements selected through said selector panel (19), said control means (21) having three functional states, a first state of which advances the program, a second state of which reverses the program and a third state of which halts the execution of said program.

2. An apparatus according to claim 2, characterized in that the control unit (18) has incorporated therein a data processor which is arranged to be initiated through the selector panel (19); and in which incorporated in the control panel (20) is a recording means (24) which is intended to record sensations of pain experienced during a sequence of movements being performed, and which is arranged to influence the program upon recording such sensations.

3. An apparatus according to claim 2, characterized in that incorporated in the control unit (18) is a register (25) which is arranged to be activated upon activation of the recording means (24), and at the end of each sequence of movements, in a manner to register pertinent factors, such as the position of the readily movable carriage means (11), and the lumbar support means (15), the tension in the tensioning means (131,131'; 132,132'; 111,111'; 30), and the pressure exerted on the lumbar support means (15).

4. An apparatus according to claim 3, characterized in that the data processor is arranged to make a comparison between factors obtained from an initial diagnosis and registered by the register (25) and factors of a program of movements carried out at the end of a treatment period.

5. An apparatus according to any one of claims 1–4, characterized in that the movable and vertically adjustable lumbar support means (15) is coupled to the readily movable carriage means (11) by means of a mechanical coupling (17; 26-28) which is effective in causing the lumbar support means (15) to take a position which conforms to the natural position of the patient's lumbar region when the carriage means (11) is made to execute a translatory or horizontal pivotal movement.

6. An apparatus according to claim 5, characterized in that the mechanical coupling includes a bush (27) which is fixedly connected to the carriage means (11); a rod (26) which is mounted on the lumbar support means (15) and which has one end thereof slidingly received in said bush and a pivot bracket (28) mounted on the lumbar support means (15) and arranged to co-act with the other end of said rod (26).

7. An apparatus according to claim 6, characterized in that the apparatus further includes guide means (40) for causing the lumbar support means (15) to maintain its position relative to the support of the chest region of the patient, when said carriage means executes a rotational movement.

8. An apparatus according to claim 7, characterized in that said guide means (40) comprises rollers, casters or like devices mounted on the undersurface of said lumbar support means (15) and arranged to run on the patient support means (10).

9. An apparatus according to any one of claims 1–4, in which the first and second tension take-up means (12,14) have the form of belts, characterized in that the tension control means includes a first pair of pulleys (112,112') mounted on at least one of said first and second tension take-up means; a second pair of pulleys (123,123') mounted on the movable carriage means (11), and a line arrangement having at least one line (111, 111') and connecting each of the pullies (112, 112') of said first pulley pair to a respective pulley (123, 123') of said second pulley pair, said at least one line having an end thereof connected to the tensioning means (30) and the other end fixedly arranged relative to either the patient support means (10) or the first or the second tension take-up means (12,14), or to the line itself.

10. An apparatus according to claim 9, characterized in that the patient support means includes a foot-end, the first pair of pulleys (112, 112') is mounted on a rigid plate (113, 113') which is affixed to said belt (12) and which extends across the whole width of said belt and protrudes somewhat beyond that edge of the belt which faces the foot-end of said patient support means (10).

11. An apparatus according to claim 10, characterized in that at least one line (111,111') has one end part passed around a guide pulley (300) arranged on the tensioning means (30) and the other end of which is secured to a post means (101,101') fixedly mounted to the patient support surface a short distance from the first tension take-up means (12) in a direction towards the foot-end of the patient support means (10).

12. An apparatus according to claim 10, characterized in that one end of said at least one line (111,111') is secured directly to the tensioning means (30), and the other end of the line is secured to a post means (101,101') fixedly mounted on the patient support means (10) a short distance from tension take-up means (12) in a direction towards the foot-end of the patient support means (10).

13. An apparatus according to claim 10, characterized in that one end of said at least one line (111,111') is secured to the tensioning means (30) in that the remaining end of said at least one line (111,111') is secured directly to said plate (113,113') and is passed around a further pulley (102,102') mounted on a post means (101,101') fixedly mounted on the patient support means (10), at a short distance from the first tension take-up means (12) in a direction towards the foot-end of said patient support means (10), and is further passed around a pulley in said first pulley pair (112,112'), around a pulley in said second pulley pair (123,123') arranged on the carriage means (11) in the proximity of said post means (101, 101').

14. An apparatus according to claim 13, characterized in that one end of said at least one line (111,111') is passed around a guide pulley (300) on the tensioning means (30) and is movably secured thereto.

15. An apparatus according to claim 13, characterized in that one end of said at least one line (111,111') is rigidly secured to said tensioning means (30).

* * * * *